United States Patent [19]
Becker et al.

[11] 4,128,529
[45] Dec. 5, 1978

[54] INDUSTRIAL BIOCIDE

[75] Inventors: Frank C. Becker, Gurnee; Jorge P. Li, Libertyville; John W. Williams, Waukegan, all of Ill.

[73] Assignee: Abbott Laboratories, North Chicago, Ill.

[21] Appl. No.: 785,905

[22] Filed: Apr. 8, 1977

[51] Int. Cl.$^2$ .................. C08K 5/34; C09D 5/14; D06M 13/40

[52] U.S. Cl. .............. 260/45.8 NB; 57/258; 106/15 R; 260/29.6 MN; 260/326.5 FM; 424/274; 427/394; 427/396; 428/907

[58] Field of Search ............. 260/45.8 NB, 326.5 FM; 106/15 R; 428/907

[56] References Cited

U.S. PATENT DOCUMENTS

| | | | |
|---|---|---|---|
| 2,205,558 | 6/1940 | Flett | 260/326.5 FM |
| 2,726,981 | 12/1955 | Wolf et al. | 260/326.5 FM |
| 2,778,825 | 1/1957 | Melamed | 106/176 |
| 2,962,504 | 11/1960 | Walker et al. | 260/326.5 FM |
| 3,394,145 | 7/1968 | Bublitz | 424/274 |
| 3,586,697 | 6/1971 | Ozaki et al. | 260/326.5 FM |
| 3,595,828 | 7/1971 | Stapfer | 260/45.7 R |
| 3,890,270 | 6/1975 | Minieri | 260/45.8 NB |
| 3,948,942 | 4/1976 | Debourge et al. | 260/326.5 FM |

OTHER PUBLICATIONS

Gagliardi, American Assoc. of Textile Chemists and Colorists, No. 2, 1962, pp. 31–40.

*Primary Examiner*—Donald E. Czaja
*Assistant Examiner*—R. A. White
*Attorney, Agent, or Firm*—Paul D. Burgauer; Robert L. Niblack

[57] ABSTRACT

By the addition of a relatively small amount of N-(phenoxyphenyl)maleimide or the corresponding 3,4-dichloromaleimide, synthetic films or plastics or woven or knitted synthetic or cellulosic fabrics can be protected against fungal and bacterial deterioration.

6 Claims, No Drawings

INDUSTRIAL BIOCIDE

DETAILED DESCRIPTION OF THE DISCLOSURE

Synthetic, film-forming materials, such as those used in the manufacture of plastic films and woven fabrics made from synthetic or cellulosic fibers are known to be subject to bacterial or fungal attacks. This is particularly known to those manufacturers whose products will be used on exterior surfaces and/or under conditions that are prone to host undesirable fungal and bacterial micro-organisms.

In order to prevent bacterial or fungal attack and consequent deterioration of the polymeric or cellulosic material so attacked or the substrate to which they are applied, manufacturers of plastic films or paints or woven fabrics have used a number of biocides on a routine basis. Many of the currently used industrial biocides are arsenicals; they are highly successful in preventing bacterial or fungal deterioration of paints and plastics. For environmental reasons, however, arsenicals are now less accepted in some of the industrial uses where biocides are needed. It has thus become highly desirable to find new, non-arsenical biocides that provide protection for polymeric substrates of all types, including film-formers, plastics, cellulosics, and the like.

It has now been found that a cellulosic, plastic or film-forming polymeric composition, knitted, woven, molded or extruded into a continuous form can be protected against bacterial or fungal attacks when they contain or are coated with between 0.005 and 5.0% by weight of N-phenoxyphenyl-maleimide or the corresponding 2,3-dichloromaleimide. These compounds are represented by the formula

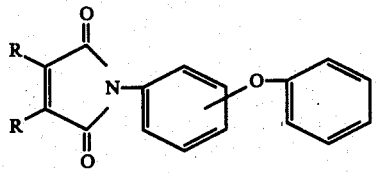

I wherein both substituents R are hydrogen or chlorine.

In many instances, the compound of formula I also inhibits the growth of bacteria or fungi in contact with the surface of the object made from a polymeric or cellulosic material containing it, particularly when said compound is persent in the higher range of the concentration recited above. In the case of a coating formulation including certain paints containing the above compound, the substrate to which it is applied is also protected. For the purpose of the present description, the term "film-forming" should be understood to refer to the polymeric particles, whether those particles are present as dry, particulate matter or in liquid, dissolved, suspended, coherent, continuous or any other form, particularly including the ultimate form for which said particles are designed. The term "plastic" is used in a similarly broad version and is to be understood to include those polymeric materials which can be extruded, injection- or compression-molded into the desired ultimate shape. The term "cellulosic" is primarily designed to refer to cotton, but also includes those cellulosic derivatives wherein the basic cellulosic structure of the fibrous material has undergone some chemical modifications that do not materially change the number of repeating units in the cellulose structure. The current process and composition will be particularly useful in fabrics made from cellulosic or olefin polymers, knitted or woven into structures exposed to outdoor conditions, such as outdoor-wear, tents, tarpaulins, and the like.

The effect of the present invention is best understood by reference to a general embodiment: To a film-forming mixture containing a synthetic polymeric material which is to be processed into a continuous phase and contains the usual ingredients, such as dyes, pigments, plasticizers, preservatives and the like, is added between 0.005 and 5.0% by weight of the compound of formula I and all ingredients are dispersed to form a homogeneous mass. Such a mixture is stable under normal storage conditions; it can be stored for extended periods of time under conditions usually required for such materials. The film or plastic article made with this mixture is then resistant to fungal or bacterial attack. This is the case whether said article is obtained by compression-molding, injection-molding, extrusion or whether it is a coating film such as obtained with the paint formulation by brushing, spray-coating or dip-coating onto the substrate and subsequent drying. These coating methods primarily are applicable where the continuous substrate is a woven or knitted cellulosic material. In most instances, the substrate and areas in contact therewith are also protected from deterioration by bacterial or fungal attack.

In order to illustrate the effect of the addition of the compound of formula I to a film-forming or plastic mixture or a woven fabric, reference is made to the following examples which, however, are not intended to limit the invention in any respect.

EXAMPLE 1

A mixture of 28 g of p-phenoxyaniline and 28 g of dichloromaleic anhydride in 200 ml of glacial acetic acid was heated at reflux for 3 hours. Upon subsequent cooling, N-phenoxyphenyl-2,3-dichloromaleimide crystallized and was collected by filtration. The 46 g (92% of theory) of crude material was washed with petroleum ether and air-dried. An analytical sample was prepared by recrystallization from glacial acetic acid, producing golden flakes of N-(p-phenoxyphenyl)-2,3-dichloromaleimide melting at 180°–181° C.

By substituting the above dichloromaleic anhydride with maleic anhydride, the corresponding N-(p-phenoxyphenyl) maleimide is obtained.

EXAMPLE 2

(a) Cotton fabric samples were soaked in an acetone solution containing N-(p-phenoxyphenyl)maleimide (hereinafter referred to as N-PM). After drying, the samples containing 0.5% by weight of N-PM are placed in nutrient agar and incubated for 24 hrs. at 37° with the bacteria named below or with mixed spores (*A.niger, A.flavus, C.globosum* and *P.funiculosum*) for 14 days at 28° C.

The same test is repeated with the above fabric samples containing the test compound, except that the samples are (b) leached for 24 hrs. in a water container regulated to a water flow providing 5 changes per hour, or (c) exposed for 24 hrs. to a Sylvania Sun lamp. The results are as follows:

| Samples | a) | b) | c) |
|---|---|---|---|
| *Staph.aureus* | N-15 | N-4 | N-6 |
| *K.pneumoniae* | N-13 | G | N-0 |

| Samples | a) | b) | c) |
|---|---|---|---|
| *E-coli* | N-1 | G | G |
| *Stv. reticulum* | NS-19 | NS-5 | NS-8 |
| Mixed spores | N-3 | N-5 | N-0 |

In this and the following tables, the entries N stand for no growth and numbers associated therewith indicate, in millimeter, the distance from the inoculation contact area which is also free of growth; G stands for growth in contact area and NS stands for no stain.

EXAMPLE 3

Fabric samples treated to contain 0.5% by weight of N-PM or 2,3-dichloro-N-PM are placed horizontally on a 4-inch layer of soil and covered with a 1-inch layer of loosely packed soil. The soil "sandwiches" are placed in a humidity cabinet for 14 days at 30° C and 90% relative humidity, and the fabrics are then inspected visually. Both fabrics are found to be in good condition, showing no signs of bacterial deterioration.

EXAMPLE 4

A basic film formulation (BF) is prepared from 100 parts of polyvinylchloride (sold by Diamond Shamrock as PVC-450), 3.5 parts of a Ba-Cd-Zn type stabilizer (Mark® KCB, marketed by Argus Chemical Corp.), 7.7 parts of epoxidized soybean oil, 40 parts of dioctyl phthalate and 0.25 parts of stearic acid. Films are prepared from (a) this formula containing the commercially recommended amount of an industrially used arsenical antibacterial (Vinyzene, marketed by the Ventron Corp.), 1% of a Ba-Cd-phosphite chelating additive (Mark® C, marketed by Argus Chemical Corp.) often used to prevent degradation due to UV exposure, and 0.65% of 4-decyloxy-2-hydroxybenzophenone, (b) BF plus 0.5% of N-PM, (c) BF plus 0.5% N-PM plus 1.0% of the above Ba-Cd-phosphite complex, (d) formula (c) plus 0.65% of 4-decyloxy-2-hydroxybenzophenone, and (e) BF plus 0.5% N-PM plus 0.65% of the benzophenone used in (d).

These samples are exposed 100, 200 or 300 hrs. in an Atlas Xenon Arc Weather-Ometer programmed for continuous light with 18 minutes of water spray every 2 hrs. The samples are placed on nutrient agar inoculated with the micro-organisms listed below and incubated as shown in Example 1. The results are shown below for the unweathered (U) and the weathered (100, 200 or 300) samples.

| Micro-Organism | Sample | a | b | c | d | e |
|---|---|---|---|---|---|---|
| *Staph.aureus* | U | N-9 | N-3 | N-3 | N-3 | N-3 |
|  | 100 | N-8 | N-3 | N-3 | N-3 | N-3 |
|  | 200 | N-5 | N-3 | N-3 | N-3 | N-3 |
|  | 300 | N-2 | N-3 | N-3 | N-3 | N-3 |
| *K.pneumoiae* | U | N-8 | G | G | G | G |
|  | 100 | N-7 | G | G | G | G |
|  | 200 | N-1 | G | G | G | G |
|  | 300 | G | G | G | G | G |
| *Stv. reticulum* | U | N-8 | N-4 | N-3 | N-4 | N-4 |
|  | 100 | N-5 | N-3 | N-3 | N-3 | N-3 |
|  | 200 | N-3 | N-3 | N-3 | N-3 | N-3 |
|  | 300 | (1) | N-3 | N-3 | N-3 | N-3 |
| Mixed spores | U | N-14 | N-0-2 | N-0-2 | N-0-2 | N-0-2 |
| (see Ex. 1) | 100 | N-8 | N-0 | N-0 | N-0 | N-0 |
|  | 200 | N-3 | N-0 | N-0 | N-0 | N-0 |
|  | 300 | (2) | N-0 | N-0 | N-0 | N-0 |

(1) = heavy growth;
(2) trace growth

In all instances, the test samples show equal or better micro-organism resistance over a commercially treated control sample (sample a) after 300 hrs. of weathering.

EXAMPLE 5

In a minimum inhibitory concentration (MIC) test, the amount of the test compound needed to prevent fungal growth is established. In this test, agar containing the test compound at a specified concentration is inoculated with 1 ml of a broth containing 10,000 units each of *A.niger* and *P.funiculosum*. The agar plates inoculated in this fashion are incubated at 30° C for 2 weeks and growth of the micro-organisms is rated on a scale of 0 to 4, with 0 indicating no growth whatsoever and 4 indicating unhibited growth.

The compound N-PM shows 0 growth at 1000 and 100 ppm concentrations, while at 10 ppm, bacterial growth does not seem to be inhibited. This indicates an MIC of about 0.005%.

In addition to the p-phenoxyphenyl compounds discussed above, the corresponding o- or m-phenoxyphenyl analogs of the above maleimide or 2,3-dichloromaleimide produce essentially identical results to the ones demonstrated above. All these position isomers are prepared in the same fashion, namely by condensing the corresponding phenoxyaniline with maleic anhydride or the corresponding 2,3-dichloromaleic anhydride.

As shown above, the present use of a new biocide is of great industrial value: The new biocide is easily prepared, and since it is active at very low concentrations as an anti-bacterial and anti-fungal agent, it will provide biocidal activity at minimal cost when applied to fabrics, plastics, fibers, coating mixtures and paints. In the case of paints, the use of the above biocide is primarily designed for the vinyl/acrylic type paints and certain oil-based paints which are less sensitive to pH variations than latex paints.

We claim:

1. A polymeric composition designed for extruding or molding into a continuous form or for application to the surface of an industrial substrate containing between 0.005 and 5.0% by weight thereof of a maleimide of the formula

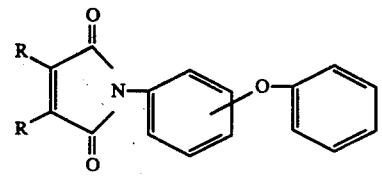

wherein both substituents R are H or Cl.

2. The composition of claim 1 wherein said maleimide is 3,4-dichloro-N-(phenoxyphenyl)maleimide.

3. The composition of claim 1 wherein said maleimide is N-(phenoxyphenyl)maleimide.

4. The method of protecting a film-forming polymeric composition or a synthetic or cellulosic fabric against bacterial or fungal attack upon extended storage or exposure environments including common bacteria or fungi, comprising adding to said composition or fabric between 0.005 and 5.0% by weight of a maleimide of the formula

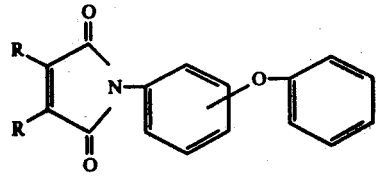

wherein both substituents R and H or Cl.

5. The process of claim 4 wherein said maleimide is 3,4-dichloro-N-(phenoxyphenyl)maleimide.

6. The process of claim 4 wherein said maleimide is N-(phenoxyphenyl)maleimide.

* * * * *